United States Patent [19]
Cavazza

[11] Patent Number: 6,063,820
[45] Date of Patent: May 16, 2000

[54] MEDICAL FOOD FOR DIABETICS

[75] Inventor: Claudio Cavazza, Rome, Italy

[73] Assignee: Sigma-Tau Industrie Farmaceutiche Riunite S.p.A., Rome, Italy

[21] Appl. No.: 09/040,341

[22] Filed: Mar. 18, 1998

[30] Foreign Application Priority Data

Mar. 20, 1997 [IT] Italy ............................... RM97A0155

[51] Int. Cl.[7] .......................... A01N 31/00; A01N 37/30; A01N 37/02; A01N 37/12
[52] U.S. Cl. .......................... 514/739; 514/556; 514/547; 514/551; 514/866
[58] Field of Search .................... 514/556, 547, 514/551, 739, 866

[56] References Cited

U.S. PATENT DOCUMENTS

| | | | |
|---|---|---|---|
| 5,037,851 | 8/1991 | Cavazza | 514/556 |
| 5,043,355 | 8/1991 | Cavazza | 514/547 |
| 5,145,871 | 9/1992 | Cavazza | 514/546 |
| 5,173,508 | 12/1992 | Cavazza | 514/547 |
| 5,192,805 | 3/1993 | Cavazza | 514/556 |
| 5,227,518 | 7/1993 | Cavazza | 560/253 |
| 5,270,472 | 12/1993 | Tagliatela et al. | 560/251 |
| 5,418,253 | 5/1995 | Cavazza et al. | 514/547 |
| 5,430,065 | 7/1995 | Cavazza | 514/556 |
| 5,432,199 | 7/1995 | Cavazza | 514/546 |
| 5,494,924 | 2/1996 | Cavazza et al. | 514/357 |
| 5,534,549 | 7/1996 | Tinti et al. | 514/556 |
| 5,591,450 | 1/1997 | Cavazza et al. | 514/547 |
| 5,614,556 | 3/1997 | Cavazza et al. | 514/546 |
| 5,627,212 | 5/1997 | Cavazza et al. | 514/547 |
| 5,637,305 | 6/1997 | Cavazza et al. | 514/547 |
| 5,639,767 | 6/1997 | Cavazza et al. | 514/547 |
| 5,747,536 | 5/1998 | Cavazza | 514/556 |
| 5,753,703 | 5/1998 | Cavazza et al. | 514/547 |

OTHER PUBLICATIONS

McCarty et al. Medical Hypotheses, 13(2) 139–51 (Abstract), 1984.

*Primary Examiner*—Theodore J. Criares
*Attorney, Agent, or Firm*—Oblon, Spivak, McClelland, Maier & Neustadt, P.C.

[57] ABSTRACT

A medical food for diabetics is disclosed which comprises as characterizing active ingredients γ-linolenic acid and at least one alkanoyl-L-carnitine, e.g. acetyl-L-carnitine and/or propionyl-L-carnitine.

15 Claims, No Drawings

MEDICAL FOOD FOR DIABETICS

MEDICAL FOOD FOR DIABETICS

The present invention relates to a therapeutic/nutritional composition (medical food) for diabetics.

Diabetes mellitus is a complex syndrome of differing genetic, environmental and pathogenetic origin.

This syndrome in any event is characterised by hyperglycaemia due to impaired insulin secretion and/or efficiency, associated with a risk of diabetic ketoacidosis or non-ketotic hyper-glycaemic-hyperosmolar coma. Among the late complications of the disease, those worthy of particular mention are nephropathy, retinopathy, atherosclerotic coronary disease, peripheral arteriopathies and neuropathies of the autonomic nervous system.

Traditionally, a distinction is made between insulin-dependent diabetes mellitus (type 1 DM) and non-insulin-dependent diabetes (type 2 DM).

Type 1 DM, which commonly develops in infancy or during adolescence, is characterised clinically by hyperglycaemia and a predisposition to diabetic ketoacidosis. Chronic insulin treatment is necessary to control the disease.

Type 2 DM is characterised clinically by hyperglycaemia not associated with a predisposition to diabetic ketoacidosis. In type 2 DM, the hyperglycaemia stems both from an abnormal insulin secretory response to glucose and from "insulin-resistance", i.e. from a reduced activity of insulin itself.

Although the therapies of choice in the therapeutic treatment of type 1 and type 2 DM, based essentially on the administration of insulin and of oral hypoglycaemic agents, yield substantial efficacy, appropriate nutritional therapy is also of major importance for the successful treatment of diabetics.

There are three key rules when tackling diabetes from the therapeutic/nutritional standpoint. First of all, diabetics need to maintain blood glucose levels as close as possible to normal values, striking the right balance between physical activity and food intake, on the one hand, and the administration of insulin and hypoglycaemic agents, on the other. Diabetics should therefore increase their intake of nutrients capable of enhancing the body's ability to metabolise glucose and insulin. Lastly, they should increase their intake of nutrients which reduce the risk of diabetic complications.

A number of micronutrients perform both the second and third functions.

Broadly speaking, the alimentary requirements of vitamins and mineral salts in diabetics under adequate metabolic control are similar to those of a normal person and should therefore comply with the amounts recommended by the Food and Nutrition Board. However, micronutrient deficiencies have been found in patients maintained on diets with a high fibre content or in those suffering from acidosis or glycosuria. Moreover, experimental evidence has suggested that vitamins, mineral salts and other micronutrients are capable of contributing towards protecting diabetic patients from complications such as heart disease, peripheral neuropathy, retinopathy, kidney failure, frequent infections and slow wound healing.

To date, particular attention has been focused upon the development of medical foods for diabetics which contribute, along with suitable pharmacological treatment, towards lowering plasma glucose levels. For example, EP 0 659 349 A1 (Bristol-Myers Squibb Co.) describes a medical food of this type in which the characterising ingredient is myo-inositol, the hypoglycaemic activity of which was, moreover, already well known.

One further characteristic of diabetes is abnormal metabolism of essential fatty acids.

Essential fatty acids such as linoleic acid and alphalinolenic acid (parent acids of the omega-6 and omega-3 essential fatty acid series, respectively) are nutritional substances which, like vitamins, have to be supplied via the diet, in that they are not biosynthesised by the body.

It has been demonstrated that the activity of omega-6-desaturase, the enzyme controlling the conversion kinetics of linoleic acid in the precursors of prostaglandins is reduced in diabetes, as are the tissue levels of essential fatty acids. The production of vascular prostacyclin also appears to be diminished.

An object of the present invention is to provide a medical food for diabetics which enables them to compensate for the reduced metabolism of essential fatty acids typical of such subjects. In particular, the object of the present invention is to provide a medical food of this type which makes it possible to by-pass the enzyme blockade caused by the reduced activity of omega-6-desaturase which occurs in diabetics and gives rise to inadequate conversion of linoleic acid into y-linolenic acid and thus to a reduced production of prostaglandin and leukotriene precursors.

The therapeutic/nutritional composition for diabetics of the present invention comprises a mixture of:

(a) γ-linolenic acid or a pharmacologically acceptable salt thereof; and (b) at least one alkanoyl-L-carnitine wherein the alkanoyl group is a straight or branched alkanoyl having 2–6 carbon atoms, or a pharmacologically acceptable salt thereof;

wherein the amounts of (a) and (b) are effective to exert a synergistic effect in compensating for the defects of the essential fatty acid metabolism and preventing diabetic complications, particularly diabetic neuropathy, and bringing about regression thereof.

Preferably, the alkanoyl-L-carnitine is selected from the group comprising acetyl-, propionyl-, butyryl-, valeryl-, and isovaleryl-L-carnitine or a pharmacologically acceptable salt thereof; acetyl-L-carnitine and propionyl-L-carnitine are particularly preferred.

What is meant by pharmacologically acceptable salts of an alkanoyl-L-carnitine are any of its salts with an acid that does not give rise to unwanted side effects. Such acids are well known to pharmacologists and to experts in pharmacy and pharmaceutical technology.

A list of FDA-approved pharmacologically acceptable acids is disclosed in Int. J. of Pharm. 33, (1986), 201–217, which is incorporated herein by reference.

The composition of the present invention may further comprise vitamins, metals, coenzymes, organic or inorganic antioxidants or precursors thereof.

Preferably, the coenzyme is coenzyme Q10, the organic antioxidant is selected from the group comprising lipoic acid, resveratrol and glutathione and a preferred precursor is N-acetyl-L-cysteine. Selenium is a preferred example of inorganic antioxidant.

A first preferred embodiment of composition according to the invention comprises in admixture the following components:

γ-linolenic acid or a pharmacologically acceptable salt thereof; acetyl-L-carnitine or a pharmacologically acceptable salt thereof;

Taurine;
Pantethine;
Vitamin A;
Vitamin E;
Vitamin $B_1$;
Vitamin $B_6$;
Vitamin $B_{12}$;
Magnesium;
Calcium;
Zinc;
Selenium;
Chromium; and
Vanadium.

A second preferred embodiment of composition further comprises coenzyme Q10, lipoic acid and myo-inositol.

A third preferred embodiment of composition comprises all the components of the first or second composition, a mixture of acetyl- and propionyl-L-carnitine (molar ratio from 10:1 to 1:10) substituting for acetyl-L-carnitine alone.

In order to be nutritionally complete, the composition of the invention can advantageously comprise also a fat source, a protein source and a carbohydrate source sufficient to meet the caloric daily need of a diabetic individual.

Preferably, this nutritionally complete composition comprises form 10 to 15% of proteins, from 35 to 45% of lipids and from 40 to 50% of carbohydrates the percentages being calculated on the overall caloric intake of the composition.

At any rate, it was found advantageous that anyone of the compositions of the present invention, suitable both for a monodose administration regimen and a multidose administration regimen, be apt to supply 350–500 mg/day of γ-linolenic acid and 1.5–2.5 mg/day of acetyl-L-carnitine.

It is unexpected and surprising that γ-linolenic acid and the alkanoyl-L-carnitine (i.e. the characterizing components of the present composition) act synergistically in enhancing the compensation of defects in essential fatty acids metabolism, or the prevention or reversal of diabetic complications, particularly diabetic neuropathy.

The further composition components are valuable for the following reasons:

Taurine, one of the most abundant amino acids in the body, is found in the central nervous system, skeletal muscles and is very concentrated in the brain and heart. Taurine deficiency is associated with retinal degeneration.

Diabetic patients have below-normal levels of taurine in blood and platelets.

Taurine administration to insulin-dependent patients was demonstrated to reduce platelet aggregation and prevent retinopathy by preventing blood clots in retinal vessels.

Pantethine is a constituent of coenzyne A, which facilitates energy production through enhancement of the metabolic pathways of fatty acid β-oxidation and the formation of acetyl-CoA.

Recent clinical trials have shown that pantethine administration to hyperlipidemic diabetic subjects was able to decrease serum total cholesterol and to increase HDL-cholesterol. Furthermore, pantethine normalized platelet volume, microviscosity and lipid composition and concomitantly reduced platelet aggregation.

Vitamin A, whose Recommended Dietary Allowance (RDA) is 1000 μg/day for adult males and 800 μg/day for adult females, has a diphasic concentration-dependent effect on insulin release. At low concentrations, vitamin A stimulates insulin release while at high concentrations it has an inhibitory effect which may be mediated in part by impairement of intracellular glucose oxidation.

Vitamin A administration to type II diabetic patients reduces insulin resistance and hastens the healing process by stimulating collagen synthesis.

The reversal of early signs of diabetic retinopathy, and apparent cessation or deceleration of the progression of more advanced proliferative retinopathy was demonstrated in diabetic patients receiving vitamin A.

The need for vitamin E whose RDA is 10 mg/day for males and 8 mg/day for females increases with higher intakes of polyunsaturated fatty acids.

Vitamin E is the most active antioxidant agent present in biological membranes where it protects cellular structures against damage from oxygen free radicals and reactive products of lipid peroxidation, thus contributing to membrane stability.

Platelet activity and eicosanoid production can be normalized by vitamin E supplementation in diabetic patients.

Vitamin B1, whose RDA is 0.5 mg/100 K calories (a minimal intake of 1 mg/day is recommended) plays a key role in energy metabolism.

The daily requirement of vitamin B1 is dependent on the intake of carbohydrates.

Vitamin B6 RDA is about 2 mg/day in normal adults.

Vitamin B6 occurs in 3 forms: pyridoxine hydrochloride, pyridoxal and pyridoxamine and is a component of approximately 120 enzymes.

In the form of pyridoxal phosphate it is a cofactor in the metabolism of amino acids and neurotransmitters and in the breakdown of glycogen; it can bind to steroid hormone receptors and can have a role in the regulation of their action.

Pyridoxine is involved in hemoglobulin formation.

Plasma vitamin B6 is often low in diabetic patients; those with poor control of blood glucose have more pronounced deficiency.

Pyridoxine deficiency in humans has been associated with glucose intolerance. The role of vitamin B6 in glucose homeostasis has been suggested by its effect on tryptophan metabolism.

Pharmacological doses of viamin B6 can reverse the abnormalities of tryptophan metabolism and may improve carbohydrate tolerance.

Vitamin B12 (RDA 2 μg/day, usual intake 4–8 μg/day) plays a pivotal role in amino acid metabolism. The B12 coenzyme catalyzes amino and fatty acid breakdown.

Vitamin B12 deficiency is associated particularly with insulin-dependent diabetes mellitus. Pernicious anemia and diabetes inellitus can occur in the same individual as part of a polyglandular autoimmune syndrome.

Magnesium (RDA 350 mg/day for adult males and 280 mg/day for females) plays an essential role in many enzymatic reactions such as the transfer of phosphate groups, the acylation of CoA and the hydrolysis of phosphate and pyrophosphate; it is important for the activation of amino acids, the aggregation of ribosomes and the synthesis and degradation of DNA.

Magnesium is involved in glucose homeostasis at multiple levels: it is a cofactor in the glucose transport system of plasma membranes; has an important role in activity of various enzymes involved in glucose oxidation, may play a role in release of insulin, and can modulate the mechanisms of energy transfer from high-energy phosphate bonds.

Diabetes mellitus is associated with increased urinary loss of magnesium especially when hyperglycemia is poorly controlled. Plasma magnesium concentration in diabetic patients is reduced. Of particular concern is the large urinary magnesium loss during diabetic ketoacidosis that causes hypomagnesemia and can induce life threatening effects on myocardium, skeletal muscles and is implicated in insulin resistance.

Magnesium deficiency has been linked to two common complications of diabetes, namely retinopathy and ischemic heart disease.

Calcium (RDA about 1 g/day for adult women and men) is the most common mineral in the human body where it has structural, electrophysiological and regulatory functions.

Diabetic patients are at increased risk for osteoporosis, presumably due to increased urinary calcium loss.

Dietary calcium competitively inhibits magnesium absorption, thus it should only be administered in conjunction with supplementary magnesium.

Zinc (RDA 15 mg/day for males and 12 mg/day for females) plays structural, enzymatic and regulatory roles. It participates to the activity of over 60 enzymes such as carboxypeptidase, carbonic anhydrase and alcohol dehydrogenase. It has a role in neuronal activity and memory and is necessary for the maintenance of normal plasma levels of Vitamin A.

Diabetes mellitus may lead to zinc deficiency. Low blood zinc and hyperzincuria have been reported in initial stages of both Type I and Type II diabetes mellitus.

Zinc is well established as playing a role in wound healing and maintenance of skin integrity because of its promoting activity in protein synthesis, cellular replication and collagen formation.

High concentrations or doses of zinc have antioxidant-like effects both in vitro and in vivo.

Selenium (RDA 70 μg/day for adult males and 55 μg/day for adult females) is an integral part of glutathione peroxidase and consequently plays a protective role against tissue damage caused by peroxides produced from lipid metabolism.

Selenium deficiency in humans causes decreased glutathione peroxidase activity and cardiomyopathy. Moreover, increased intakes of selenium may reduce the risk of cardiovascular diseases, reverses early signs of diabetic retinopathy, and brings about apparent cessation or deceleration of the progression of more advanced proliferative retinopathy.

Chromium's Estimated Safe and Adiquate Daily Dietary Intake (ESADDI) for adults of both sexes is from 50 to 200 mg/day.

Chromium is an essential nutrient required for normal carbohydrate and lipid metabolism. It is a component of the biological active glucose-tolerance factor whose deficiency is implicated in the pathogenesis of some forms of glucose intolerance and diabetes mellitus.

Urinary chromium excretion tends to increase in diabetics.

Vanadium's ESADDI is about 100 μg/day; bioavailability is very low, generally less than 1%.

Vanadium has an insulin-like behavior in insulin-dependent diabetics. It either mimics the effects of insulin or increases its efficiency, reducing both glucose and insulin levels.

The administration of vanadium to type II diabetic patients improves glucose tolerance, lowers blood glucose levels and decreases blood cholesterol levels.

I claim:

1. A therapeutic/nutritional composition, comprising a mixture of:
   (a) γ-linolenic acid or a pharmacologically acceptable salt thereof; and
   (b) at least one alkanoyl-L-carnitine in which the alkanoyl group is a straight or branched alkanoyl group having 2–6 carbon atoms, or a pharmacologically acceptable salt thereof, which components act synergistically to enhance the compensation for defects in essential fatty acid metabolism of a diabetic or preventing or reversing diabetic neuropathy.

2. The composition of claim 1, wherein the alkanoyl-L-carnitine is selected from the group comprising acetyl-, propionyl-, butyryl-, valeryl-, and isovaleryl-L-carnitine or a pharmacologically acceptable salt thereof.

3. The composition of claim 1, which comprises acetyl-L-carnitine and propionyl-L-carnitine or the pharmacologically acceptable salts thereof, wherein their molar ratio is 10:1 to 1:10.

4. The composition of claim 1, further comprising vitamins and metals.

5. The composition of claim 4 which comprises a mixture of the following components:

γ-linolenic acid or a pharmacologically acceptable salt thereof;

acetyl-L-carnitine or a pharmacologically acceptable salt thereof;

the linolenic acid and acetyl-L-carnitine being present in synergistic effective amounts;

Taurine;

Pantethine;

Vitamin A;

Vitamin E;

Vitamin $B_1$;

Vitamin $B_6$;

Vitamin $B_{12}$;

Magnesium;

Calcium;

Zinc;

Selenium;

Chromium; and

Vanadium.

6. The composition of claim 5, which comprises acetyl-L-carnitine and propionyl-L-carnitine or the pharmacologically acceptable salts thereof wherein their molar ratio is 10:1 to 1:10.

7. The composition of claim 1, which further comprises a coenzyme and/or an inorganic or organic antioxidant or a precursor thereof.

8. The composition of claim 7, wherein the coenzyme is coenzyme Q10, the organic antioxidant is selected from the group comprising lipoic acid, resveratrol or glutathione and the precursor is N-acetyl-L-cysteine.

9. The composition of claim 5, which further comprises coenzyme Q10, lipoic acid and myo-inositol.

10. The composition of claim 1 as a nutritionally complete composition further comprising a lipid component, a protein component and a carbohydrate component, suitable to provide the caloric daily intake needed by a diabetic individual.

11. The composition of claim 10 which comprises from 10 to 15% of proteins, from 35 to 45% of lipids and from 40 to 50% of carbohydrates, the percentages being calculated on the overall caloric intake of the composition.

12. The composition of claim 1 suitable to supply, in a single or multiple dose administration regimen, from about 350 to 500 mg/day of γ-linolenic acid and from 1.5 to 2.5 g/day of acetyl-L-carnitine.

13. A method for compensating for defects of essential fatty acid metabolism in diabetics, comprising:

administering synergistic effective amounts of a therapeutic/nutritional composition comprising a mixture of:

(a) γ-linolenic acid or a pharmacologically acceptable salt thereof; and
(b) at least one alkanoyl-L-carnitine, wherein the alkanoyl group is a $C_{2-6}$ straight or branched alkanoyl group or a pharmacologically acceptable salt thereof, to a subject suffering from diabetes.

14. A method of preventing diabetic complications, comprising:

administering synergistic effective amounts of a therapeutic/nutritional composition comprising a mixture of:

(a) γ-linolenic acid or a pharmacologically acceptable salt thereof; and
(b) at least one alkanoyl-L-carnitine, wherein the alkanoyl group is a $C_{2-6}$ straight or branched alkanoyl group or a pharmacologically acceptable salt thereof, to a subject suffering from diabetes.

15. The method of claim 14, wherein said diabetic complication is diabetic neuropathy.

* * * * *

UNITED STATES PATENT AND TRADEMARK OFFICE
CERTIFICATE OF CORRECTION

PATENT NO. : 6,063,820             Page 1 of 1
DATED : May 16, 2000
INVENTOR(S) : Claudio Cavazza It is certified that error appears in the above-identified patent and that said Letters Patent is hereby corrected as shown below:

<u>Column 3,</u>
Line 33, "1.5-2.5 mg/day" should read -- 1.5-2.5 g/day --

Signed and Sealed this

Ninth Day of April, 2002

Attest:

*Attesting Officer*

JAMES E. ROGAN
*Director of the United States Patent and Trademark Office*